(12) United States Patent
Im et al.

(10) Patent No.: US 9,642,929 B2
(45) Date of Patent: May 9, 2017

(54) CARBOXYLMETHYL CELLULOSE FOAM FOR HEMOSTASIS AND WOUND TREATMENT, AND METHOD FOR PREPARING SAME

(71) Applicant: KOREA INSTITUTE OF INDUSTRIAL TECHNOLOGY, Chungcheongnam-do (KR)

(72) Inventors: Jung Nam Im, Gyeonggi-do (KR); Song Jun Doh, Gyeonggi-do (KR); Tae Hee Kim, Gyeonggi-do (KR); Min Ji Yoon, Gyeonggi-do (KR); Chae Hwa Kim, Seoul (KR)

(73) Assignee: Korea Institute of Industrial Technology, Chungcheongnam-Do (KR)

( * ) Notice: Subject to any disclaimer, the term of this patent is extended or adjusted under 35 U.S.C. 154(b) by 90 days.

(21) Appl. No.: 14/782,843

(22) PCT Filed: Nov. 20, 2013

(86) PCT No.: PCT/KR2013/010545
§ 371 (c)(1),
(2) Date: Oct. 7, 2015

(87) PCT Pub. No.: WO2014/168307
PCT Pub. Date: Oct. 16, 2014

(65) Prior Publication Data
US 2016/0067370 A1 Mar. 10, 2016

(30) Foreign Application Priority Data
Apr. 8, 2013 (KR) .......................... 10-2013-0038336

(51) Int. Cl.
| | | |
|---|---|---|
| *A61L 15/28* | (2006.01) |
| *A61L 15/42* | (2006.01) |
| *A61F 13/00* | (2006.01) |
| *A61L 15/60* | (2006.01) |
| *A61F 13/15* | (2006.01) |
| *A61L 15/44* | (2006.01) |

(52) U.S. Cl.
CPC ........ *A61L 15/28* (2013.01); *A61F 13/00012* (2013.01); *A61F 13/15203* (2013.01); *A61L 15/425* (2013.01); *A61L 15/44* (2013.01); *A61L 15/60* (2013.01); *A61F 2013/15463* (2013.01); *A61L 2300/404* (2013.01); *A61L 2300/418* (2013.01); *A61L 2400/04* (2013.01)

(58) Field of Classification Search
CPC ........... A61L 15/28; A61L 15/42; A61F 13/00
USPC ......................................................... 514/57
See application file for complete search history.

(56) References Cited

U.S. PATENT DOCUMENTS 4,200,737 A  4/1980 Marder et al.

FOREIGN PATENT DOCUMENTS

| JP | 2008-013510 A | 1/2008 |
| JP | 2010-284216 A | 12/2010 |
| KR | 10-2002-0062301 A | 7/2002 |
| KR | 10-2003-0055102 A | 7/2003 |

*Primary Examiner* — Sudhakar Katakam
*Assistant Examiner* — Everett White
(74) *Attorney, Agent, or Firm* — McNees Wallace & Nurick LLC

(57) ABSTRACT

The present invention relates to a highly liquid absorbent and hardly water-soluble carboxymethyl cellulose (CMC) foam, which absorbs body fluid or water, expands in volume when absorbing liquid, does not gelate, and maintains shape. The hardly water-soluble CMC foam prepared according to the preparation method of the present invention has remarkably superior liquid absorption property, shows large volume expansibility when absorbing liquid, does not gelate, and maintains shape. Therefore, a remarkably improved ability is shown when used as a hemostatic agent and a wound dressing. In addition, when the CMC foam is treated with a CMC powder dispersing liquid, the surface characteristics change, thereby preventing adhesion with the skin and improving liquid retention capability. Thus, it is possible to control the liquid absorption property thereof to meet the desired purpose.

15 Claims, 2 Drawing Sheets

CARBOXYLMETHYL CELLULOSE FOAM FOR HEMOSTASIS AND WOUND TREATMENT, AND METHOD FOR PREPARING SAME

BACKGROUND OF THE INVENTION

1. Field of the Invention

The present invention relates to highly absorbent, water-insoluble carboxymethyl cellulose foam, which expands in volume when absorbing liquid or water, but does not gelate, and maintains shape.

2. Description of the Related Art

Carboxymethyl cellulose, usually called CMC, is a cellulose derivative in which the hydroxyl groups of glucose, which makes up the cellulose backbone, are substituted with carboxymethyl groups. CMC is used in various fields including glues, foods, cosmetics, additives for pharmaceutical drugs, petroleum drilling, etc., and in particular, it is widely used in medical products due to its excellent biocompatibility.

Examples of medical applications of CMC include adhesion barriers, wound healing agents, hemostatic agents, etc. Importantly, adhesion barriers should be decomposed after a certain period of time once they are inserted into the body, whereas wound healing agents and hemostatic agents for external wound, should maintain their shapes for a certain period of time without being decomposed. Accordingly, water-insolubility is a prerequisite for use as external wound healing agents or hemostatic agents.

Importantly, CMC foam should have high degree of liquid absorption for a medical use. In the case of a moisture wound dressing, it is important to effectively absorb body fluids produced during wound healing, and the foam to be used for this purpose should be highly absorbent. For a hemostatic dressing, the foam to be used for this purpose should also be highly absorbent in order to sufficiently absorb the blood being released.

Additionally, when the CMC foam absorbs liquid it is desirable that the CMC foam expands in volume while maintaining its shape. The volumetric expansion due to the absorption of body fluids during a wound healing process can reduce the dead space between a wound dressing and the wound surface, and therefore prevent invasion of infectious agents, such as bacteria, into the wound surface. Additionally, in the case of a cavity dressing, the dressing size is preferably small for easy insertion into the wound cavity. The dressing, once correctly placed on the cavity, can absorb body fluids or a saline solution to expand its volume, thereby filling up the cavity. If used as a hemostatic agent, the dressing can expand its volume by absorbing blood, thereby compressing blood vessels and promoting hemostasis.

Accordingly, for medical use of the CMC foam, and in particular, for its use as a wound healing agent or a hemostatic agent, it is important that the CMC foam has the properties of water-insolubility, high degree of liquid absorption, and high expansibility. However, the CMC foams known so far had problems in that they have a poor expansibility of about 1.5-fold (150%) or they gelate after absorbing a liquid and are thus unable to maintain their shapes.

For example, Korean Patent No. 10-0588614 and Japanese Patent Application Publication No. 2010-284216 describe anti-adhesion agents comprising CMC as an active ingredient. However, CMC was used as an anti-adhesion agent in the above patent documents, and it is not suitable for use as a wound healing agent or a hemostatic agent because it decomposes after a certain period of time when inserted into the body, and gelates when absorbing a liquid.

Additionally, Korean Patent Application Publication No. 2002-0062301 describes a tissue-coating medical material made of a soluble cellulose derivative that has been made hardly soluble in water. However, this patent document fails to describe the liquid absorption and volume expansion of the material, and is thus not suitable for use as a dressing, etc.

SUMMARY OF THE INVENTION

The inventors of the present invention, while endeavoring to develop a highly absorbent, water-insoluble cellulose derivative foam having an expansive characteristic when in contact with a body fluid or water, discovered that when CMC foam is prepared by freeze-drying followed by an appropriate acid treatment and compression, the resulting foam has a markedly increased degree of liquid absorption, does not gelate when absorbing liquid and maintains its shape, and exhibits high volumetric expansion, thereby completing the present invention.

Accordingly, an object of the present invention is to provide water-insoluble CMC foam, which has degree of liquid absorption of 20 g/g or higher when applied a 0.9% saline solution, and has a 2-fold (200%) or higher volume expansion, due to expansion in thickness, after absorbing the saline solution compared to that before absorbing the saline solution.

Preferably, the water-insoluble CMC foam has a 3-fold (300%) or higher volume expansion, due to expansion in thickness, after absorption of a saline solution compared to that before absorbing the saline solution, and more preferably a 3-fold (300%) or higher volume expansion. The extent of volume expansion may be controlled by the degree of compression in the preparation method of the present invention, to be set forth herein below.

Additionally, the present invention provides a method of preparing water-insoluble CMC foam that does not gelates when absorbing liquid, including: (1) preparing CMC foam by freeze-drying a CMC solution, in which 1 wt % to 2 wt % of CMC powder is dissolved; (2) acid-treating the foam prepared in step 1 by immersing the foam in an acid solution, and then heating; and (3) compressing the acid-treated foam in Step 2 at 60° C. or below.

Additionally, the present invention provides a method of preparing water-insoluble CMC foam, which further includes Step 2-1 of immersing the acid-treated foam in the dispersion containing CMC powder in liquid, between Step 2 and Step 3.

The present invention is described in detail herein below.

The present inventors discovered that when CMC powder is prepared into foam by freeze-drying and then subjected to acid treatment and compression at an appropriate temperature, the resulting foam is provided with water-insolubility, high degree of liquid absorption and volume expansion, but maintains its shape without gelation. In particular, the present inventors also confirmed that, for provision of water-insolubility, the acid treatment should be conducted at room temperature or higher, and also the compression should be performed at or below an appropriate temperature (60° C.) in order to optimize the degree of liquid absorption and expansion rate, and the degree of liquid absorption under pressure.

Additionally, the present inventors confirmed that when the foam is treated further by immersing it in a dispersion containing CMC powder in liquid, between the acid treatment and compression, the resulting foam has smooth surface due to gelation when in contact with water or a body fluid, while maintaining the shape of the foam due to presence of the aqueous CMC powder component treated on the water-insoluble foam, thus not being attached to the surface of a wound, and improving the degree of liquid absorption, and the degree of liquid absorption under pressure. The present invention is based on these findings.

According to one aspect, the present invention provides water-insoluble CMC foam, which has a degree of liquid absorption of 20 g/g or higher when applied a 0.9% saline solution, and has a 2-fold (200%) or higher volume expansion, due to expansion in thickness, after absorbing the saline solution compared to that before absorbing the saline solution, preferably 3-fold (300%) or higher, and more preferably 4-fold (400%) or higher.

For the medical use of the water-insoluble CMC foam of the present invention, such as a hemostatic agent and a wound healing agent, it is important that the water-insoluble CMC foam have high degree of liquid absorption when put into a saline solution. As used herein, the term "0.9% saline solution" refers to an isotonic solution prepared based on the idea that the NaCl concentration in human body fluid is 0.9%.

The CMC foam of the present invention showed a degree of liquid absorption of 20 g/g or higher when applied a 0.9% saline solution, which is a markedly improved the degree of liquid absorption compared to that of the existing foam.

Additionally, the water-insoluble CMC foam of the present invention has a 2-fold (200%) or higher volume expansion, due to expansion in thickness, after absorbing the saline solution compared to that before absorbing the saline solution, preferably 3-fold (300%) or higher, and more preferably 4-fold (400%) or higher, and is thus suitable for use as a wound healing agent or a hemostatic agent.

Additionally, the present invention provides a method of preparing water-insoluble CMC foam, which has a degree of liquid absorption of 20 g/g or higher when applied a 0.9% saline solution, and also has a 4-fold (400%) or higher volume expansion, due to expansion in thickness, after absorbing the saline solution compared to that before absorbing the saline solution. That is, the present invention provides a method of preparing water-insoluble CMC foam including: (1) preparing CMC foam by freeze-drying a solution, in which 1 wt % to 2 wt % of CMC powder is dissolved; (2) acid-treating the foam prepared in step 1 by immersing the foam in an acid solution, and then heating; and (3) compressing the acid-treated foam in Step 2 at 60° C. or below.

Step 1 above is a step for preparing CMC foam by subjecting the solution, in which CMC powder is dissolved, to freeze-drying. The solution in Step 1 is prepared by dissolving CMC powder in water, and preferably by dissolving in distilled water.

Preferably, the degree of substitution of the CMC powder used in the dissolution should be 0.4 or higher. In an exemplary embodiment of the present invention, CMC powder having a degree of substitution of 0.5 was used.

Preferably, the concentration of the CMC solution prepared above should be in the range of 1 wt % to 2 wt %. When the concentration of the CMC solution is lower than 1 wt % the physical strength of the thus-prepared foam becomes deteriorated, whereas when the concentration of the CMC solution is higher than 2 wt % the viscosity of the CMC solution increases, thereby making it difficult to prepare uniform foam.

The freeze-drying may be performed by a conventional method known to those skilled in the art. In an exemplary embodiment of the present invention, the freeze-drying was performed by freezing at −10° C. followed by drying under vacuum.

Step 2 above is a step for acid treatment of the foam prepared in step 1 by immersing the foam in an acid solution, and then heating, and water-insolubility is provided to the foam by the acid treatment. In particular, the acid solution may be prepared by adding an acid to a mixture containing an alcohol and water; or adding an acid to an alcohol alone. The acid to be added may be at least one selected from the group consisting of lactic acid, acetic acid, citric acid, succinic acid, formic acid, and hydrochloric acid, but is not limited thereto. The alcohol may be at least one selected from the group consisting of ethanol, methanol, isopropanol, etc., but is not limited thereto.

When the mixture containing an alcohol and water is used as an acid solution, the volume ratio of the alcohol is preferably in the range of 60% to 100%, and more preferably, 80% to 100%. When the alcohol component accounts for less than 60%, gelation of the foam may occur due to excessively existing water during the acid treatment, and the pores inside the foam may be clogged or deformed in shape.

In the acid treatment in Step 2, the heat treatment is preferably performed in the range of 40° C. to 70° C. When the acid treatment is performed at room temperature, the treated foam cannot have enough water-insolubility. Therefore, it is important to apply heat so that the water-insolubility could be provided to the foam.

Step 3 above is a step for compressing the acid-treated foam prepared in Step 2. The foam, which was reduced in its volume by compression, can expand in volume when in contact with water or a body fluid by absorbing the liquid, and thus can exhibit an effective hemostatic effect when applied to cavities during surgeries. The existing products have only a negligible volume expansion rate of about 1.5-fold (150%), whereas the foams prepared by the present invention had the volume expansion of 2-fold (200%) or higher in thickness, preferably 3-fold (300%) or higher, and more preferably 4-fold (400%) or higher, thus confirming the improved functions.

Preferably, the above compression should be performed at 60° C. or below. When the compression temperature is above 60° C., the degree of liquid absorption, expansion rate, and the degree of liquid absorption under pressure become drastically decreased.

As described above, the volume expansion rate may be controlled depending on the desired products by adjusting the degree of compression. In the present invention, CMC foam is prepared by freeze-drying a solution, in which CMC powder is dissolved (Step 1), and thus porous CMC foam can be prepared, and the porosity of the CMC foam can be maintained in Steps 2 and 3. In particular, after compression in Step 3, the porosity can still be maintained although the size of the pores varies, and thus a high volume expansion property can be retained when absorbing liquid. Since the porosity can be maintained, the desired volume expansion rate can easily be controlled by the degree of compression, for example, in order to obtain a 4-fold (400%) volume expansion rate, the thickness can be compressed to 25% of the original thickness. When the thus-prepared water-insoluble CMC foam is immersed in a saline solution, the saline solution is absorbed into the compressed pores to recover the original volume, and as such, the water-insoluble CMC foam can exhibit an excellent function when used as a wound healing agent or a hemostatic agent.

Additionally, the present invention provides a method of preparing water-insoluble CMC foam including (1) preparing CMC foam by freeze-drying a solution, in which 1 wt % to 2 wt % of CMC powder is dissolved; (2) acid-treating the foam prepared in step 1 by immersing the foam in an acid solution, and then heating; and (3) compressing the acid-treated foam in Step 2 at 60° C. or below, wherein the method further includes Step 2-1 of immersing the acid-treated foam in the dispersion containing CMC powder in liquid, between Step 2 and Step 3.

The thus-prepared water-insoluble CMC foam has a degree of liquid absorption of 20 g/g or higher when put into a 0.9% saline solution, and also has a 2-fold (200%) or higher expansion in volume after absorbing the saline solution compared to that before absorbing the saline solution, preferably 3-fold (300%) or higher, and more preferably 4-fold (400%) or higher.

Step 2-1 above is a step for immersing the acid-treated foam prepared in Step 2-1 in a dispersion containing CMC powder in liquid, and by this step, the surface characteristics undergo change. Since the CMC contained in the dispersion in liquid is water-soluble, the surface of the foam treated with the dispersion, when in contact with water or a body fluid, gelates, thereby making the surface smooth. This is an advantage in that the surface of the foam, when applied to the surface of a wound, gelates and thus is prevented from being attached to the wound surface. Since the gelation of the water-soluble CMC added proceeds on the surface while the water-insoluble foam maintains the overall shape, the adhesion between the foam and the wound surface can be reduced while the overall shape is maintained, when liquid is absorbed thereto.

Additionally, the foam treated with the dispersion solution showed improvements in a degree of liquid absorption and a degree of liquid absorption under pressure, due to the gelation of the water-soluble CMC. Accordingly, the degree of liquid absorption and the degree of liquid absorption under pressure of the foam can be controlled as desired, according to the degree of the dispersion treatment.

The dispersion containing CMC in liquid may be prepared by dispersing CMC powder in at least one solvent selected from the group consisting of ethanol, methanol, and isopropanol. The mixing ratio between the solvent for the dispersion and the CMC powder may be appropriately adjusted, and preferably at a ratio of 160 g of the solvent per 1 g of CMC powder.

Additionally, the present invention provides a method of preparing water-insoluble CMC foam including (1) preparing CMC foam by freeze-drying a solution, in which 1 wt % to 2 wt % of CMC powder is dissolved; (2) acid-treating the foam prepared in step 1 by immersing the foam in an acid solution, and then heating; and (3) compressing the acid-treated foam in Step 2 at 60° C. or below, and optionally including Step 2-1 of immersing the acid-treated foam in the dispersion containing CMC powder in liquid, between Step 2 and Step 3.

The water-insoluble CMC foam of the present invention has a degree of liquid absorption of 20 g/g or higher. When immersed in a 0.9% saline solution, the water-insoluble CMC foam of the present invention has significantly improved a degree of liquid absorption of 20-fold or higher, whereas conventional polyurethane foams have a degree of liquid absorption of 15-fold or below of their weight. Accordingly, the foam of the present invention can exert an excellent effect if used as a wound healing agent or a hemostatic agent.

Additionally, the water-insoluble CMC foam of the present invention can undergo a 4-fold (400%) or higher volume expansion when absorbing liquid. While the conventional commercialized foams have a maximum of about 1.5-fold (150%) volume expansion, the foam of the present invention was improved to have a 2-fold (200%) or higher volume expansion rate by compression at an appropriate condition, preferably 3-fold (300%) or higher, and more preferably 4-fold (400%) or higher.

The water-insoluble CMC foam of the present invention may be provided with an antibacterial activity by combining with an antibacterial agent. Examples of the antibacterial agents to be combined may be at least one selected from the group consisting of silver, silver-based compounds, biguanides, and methylene blue, but are not limited thereto.

The water-insoluble CMC foam of the present invention may be fortified with a hemostatic function by combining with a hemostatic material. Examples of the hemostatic materials to be combined may be collagen, gelatin, thrombin, etc., but are not limited thereto.

In an exemplary embodiment, the present invention provides a wound healing agent prepared using the water-insoluble CMC foam. Since the water-insoluble CMC foam has excellent liquid absorption property, and a high volume expansion rate when absorbing liquid, if it is used as a wound healing agent it can expand during use, thereby effectively preventing bacterial contamination. Additionally, when the water-insoluble CMC foam of the present invention is applied to body cavities, it can easily be introduced into the body due to its small size, which has been reduced by compression, and once introduced into the body, it can absorb body fluid and expand, and effectively fill in the cavities.

In an exemplary embodiment, the present invention provides a hemostatic agent prepared using the water-insoluble CMC foam. Since the water-insoluble CMC foam has excellent liquid absorption property, if it is used as a hemostatic agent it can exhibit a markedly improved function, compared to that of the conventional hemostatic agents. Additionally, when absorbing liquid, it expands in volume and compresses blood vessels, thereby promoting hemostasis.

Advantageous Effect of the Invention

The water-insoluble CMC foam prepared according to a method of the present invention has extremely excellent liquid absorption property, high volume expansion rate when absorbing liquid, and maintains its shape without gelation. Accordingly, if used as a hemostatic agent and a wound healing agent, it can exhibit markedly improved functions. Additionally, if the CMC foam is treated with a dispersion containing CMC powder in liquid, it changes the surface characteristics of the CMC foam, thereby preventing its adhesion to the skin, and increasing the degree of liquid absorption under pressure. Accordingly, the degree of liquid absorption can be controlled according to the intended purposes.

DETAILED DESCRIPTION OF THE PREFERRED EMBODIMENTS

Figure 1:
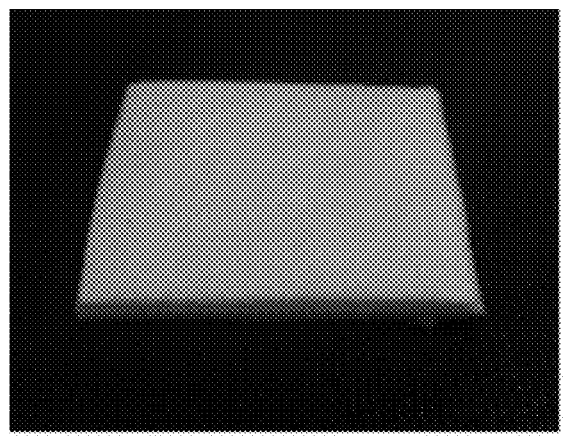
FIG. 1 is a picture of foam prepared according to a method of the present invention.

Hereinafter, the present invention will be described in more detail with reference to exemplary Examples. However, these Examples are for illustrative purposes only, and the invention is not intended to be limited by these Examples.

Example 1

CMC powder (degree of substitution: 0.5) was dissolved in distilled water and 1.5 wt % CMC solution was prepared. The viscosity of the thus-prepared solution was 4,315 cps. The solution was poured into a frame with a predetermined size and frozen at −10° C. for 24 hours. The frozen solution was vacuum-dried to prepare foam with a density of 0.02 g/cm$^3$. The thus-prepared foam was immersed in a mixture of ethanol (200 g) and 35% HCl (10 mL), and heated at 50° C. for 2 hours while stirring. The foam was thoroughly washed with ethanol and dried in a vacuum oven kept at 70° C. The dried foam was compressed at room temperature to prepare 1 mm-thick foam.

Example 2

One millimeter-thick foam was prepared in the same manner as in Example 1, except for using a mixture of ethanol (200 g) and 85% lactic acid (38.5 g) as a solution for acid treatment.

Example 3

One millimeter-thick foam was prepared in the same manner as in Example 2, except for compressing the dried foam at 40° C. instead of room temperature.

Example 4

One millimeter-thick foam was prepared in the same manner as in Example 2, except for compressing the dried foam at 60° C. instead of room temperature.

Example 5

CMC powder (degree of substitution: 0.5) was dissolved in distilled water and a 1.5 wt % CMC solution was prepared. The viscosity of the thus-prepared solution was 4,315 cps. The solution was poured into a frame with a predetermined size and frozen at −10° C. for 24 hours. The frozen solution was vacuum-dried to prepare foam with a density of 0.02 g/cm$^3$. The thus-prepared foam was immersed in a mixture, in which citric acid (2.2 g) was dissolved in a mixture of methanol (160 mL) and distilled water (40 mL), and heated at 65° C. for 2 hours while stirring. The foam was thoroughly washed with ethanol and dried in a vacuum oven kept at 70° C. The dried foam was compressed at room temperature to prepare 1 mm-thick foam.

Example 6

CMC powder (degree of substitution: 0.5) was dissolved in distilled water and a 1.5 wt % CMC solution was prepared. The viscosity of the thus-prepared solution was 4,315 cps. The solution was poured into a frame with a predetermined size and frozen at −10° C. for 24 hours. The frozen solution was vacuum-dried to prepare foam with a density of 0.02 g/cm$^3$. The thus-prepared foam was immersed in a mixture of ethanol (200 g) and 35% HCl (10 mL), and heated at 50° C. for 2 hours while stirring. Then, the foam was thoroughly washed with ethanol and dried in a vacuum oven kept at 70° C. The dried foam was immersed in a mixed dispersion of methanol (160 g) and CMC powder (1 g), and stirred for 10 minutes. The treated foam was taken out and dried in a vacuum oven kept at 70° C. The dried foam was compressed at room temperature to prepare 1 mm-thick foam.

Example 7

One millimeter-thick foam was prepared in the same manner as in Example 6, except for using a mixture of ethanol (200 g) and 85% lactic acid (38.5 g) as a solution for acid treatment.

Example 8

One millimeter-thick foam was prepared in the same manner as in Example 7, except for compressing the dried foam at 40° C. instead of room temperature.

Example 9

One millimeter-thick foam was prepared in the same manner as in Example 7, except for compressing the dried foam at 60° C. instead of room temperature.

Example 10

CMC powder (degree of substitution: 0.5) was dissolved in distilled water and a 1.5 wt % CMC solution was prepared. The viscosity of the thus-prepared solution was 4,315 cps. The solution was poured into a frame with a predetermined size and frozen at −10° C. for 24 hours. The frozen solution was vacuum-dried to prepare foam with a density of 0.02 g/cm$^3$. The thus-prepared foam was immersed in a mixture, in which citric acid (2.2 g) was dissolved in a mixture of methanol (160 mL) and distilled water (40 mL), and heated at 65° C. for 2 hours while stirring. The foam was thoroughly washed with ethanol and dried in a vacuum oven kept at 70° C. The dried foam was immersed in a mixed dispersion of methanol (320 g) and CMC powder (2 g), and stirred for 10 minutes. The treated foam was taken out and dried in a vacuum oven kept at 70° C. The dried foam was compressed at room temperature to prepare 1 mm-thick foam.

Comparative Example 1

CMC powder (degree of substitution: 0.5) was dissolved in distilled water and a 1.5 wt % CMC solution was prepared. The viscosity of the thus-prepared solution was 4,315 cps. The solution was poured into a frame with a predetermined size and frozen at −10° C. for 24 hours. The frozen solution was vacuum-dried to prepare foam with a density of 0.02 g/cm$^3$. The thus-prepared foam was immersed in a mixture of pH 2.5, prepared by adding HCl to ethanol (200 g), and treated therein at room temperature for 6 hours. Then, the foam was thoroughly washed with ethanol and dried in a vacuum oven kept at 70° C. The dried foam was compressed at 120° C. to prepare 1 mm-thick foam.

Comparative Example 2

One millimeter-thick foam was prepared in the same manner as in Example 2, except for compressing the dried foam at 80° C. instead of room temperature.

Comparative Example 3

One millimeter-thick foam was prepared in the same manner as in Comparative Example 2, except for compressing the dried foam at 100° C. instead of room temperature.

Comparative Example 4

One millimeter-thick foam was prepared in the same manner as in Comparative Example 2, except for compressing the dried foam at 120° C. instead of room temperature.

The characteristics of foams prepared in Experimental Examples 1 to 10 and Comparative Examples 1 to 4 are summarized in Table 1 below.

TABLE 1

| | Acid Type | Temp. for Acid Treatment (° C.) | Immersion of dispersion containing CMC powder in liquid | Compression Temp (° C.) |
|---|---|---|---|---|
| Example 1 | HCl | 50 | x | Room Temp. |
| Example 2 | Lactic acid | 50 | x | Room Temp. |
| Example 3 | Lactic acid | 50 | x | 40 |
| Example 4 | Lactic acid | 50 | x | 60 |
| Example 5 | Citric acid | 65 | x | Room Temp. |
| Example 6 | HCl | 50 | o | Room Temp. |
| Example 7 | Lactic acid | 50 | o | Room Temp. |
| Example 8 | Lactic acid | 50 | o | 40 |
| Example 9 | Lactic acid | 50 | o | 60 |
| Example 10 | Citric acid | 65 | o | Room Temp. |
| Comparative Example 1 | HCl | Room Temp. | x | 120 |
| Comparative Example 2 | Lactic acid | 50 | x | 80 |
| Comparative Example 3 | Lactic acid | 50 | x | 100 |
| Comparative Example 4 | Lactic acid | 50 | x | 120 |

Experimental Example 1: Analysis of Characteristics According to Acid Treatment

Figure 2:
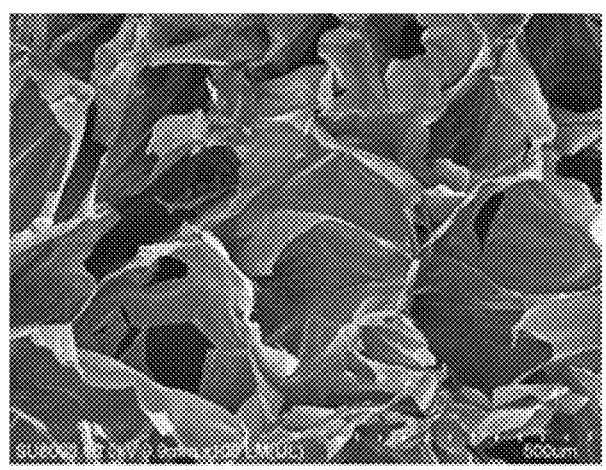
FIG. 2 is a picture by scanning electron microscope of foam prepared according to a method of the present invention.

For the analysis of characteristics of CMC foams depending on acid treatment during CMC foam preparation, the foams prepared in Example 1 and Comparative Example 1 were immersed in a 0.9% saline solution for 10 minutes. The image of CMC foam prepared in Example 1 before immersion is shown in FIG. 1 and the morphology by scanning electron microscope is shown in FIG. 2.

The foams prepared in Example 1 and Comparative Example 1 were immersed in a 0.9% saline solution for 10 minutes and the changes in their shapes were observed. The respective images are shown in FIGS. 3 and 4.

Figure 3:
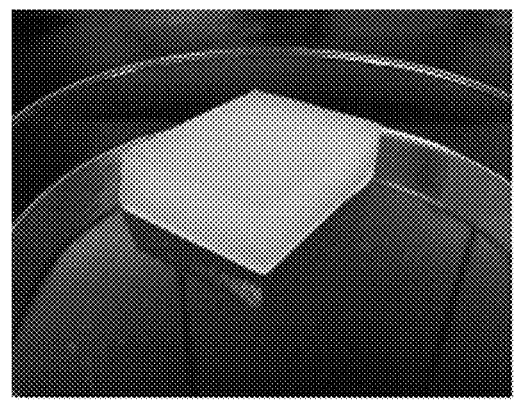
FIG. 3 is a picture of foam prepared according to a method of the present invention, which was expanded by immersing in a 0.9% saline solution for 10 minutes.
Figure 4:
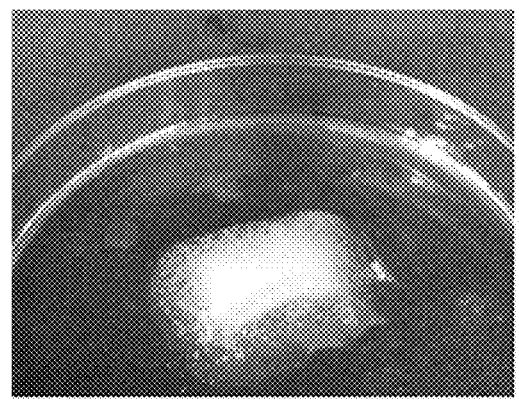
FIG. 4 is a picture of foam prepared according to a method of Comparative Example 1 of the present invention, which gelated by immersing in a 0.9% saline solution for 10 minutes.

As shown in FIG. 3, the CMC foam prepared in Example 1, which was subjected to acid treatment by heating, was swollen after liquid absorption, and its shape was maintained. However, the CMC foam prepared in Comparative Example 1, which was subjected to acid treatment at room temperature, gelated after liquid absorption, and failed to show its shape stability.

Experimental Example 2: Analysis of Characteristics Depending on Compression Temperature For the analysis of characteristics of CMC foams depending on the temperature of compression process during CMC foam preparation, the thickness expansion rate and the degree of liquid absorption of the CMC foams prepared in Examples 2 to 4, which were compressed at room temperature, 40° C., and 60° C., respectively, and the CMC foams prepared in Comparative Examples 2 to 4, were measured.

The thickness expansion rate indicates the ratio between the original thickness and the swollen thickness after liquid absorption, and the above-prepared foams were immersed in a 0.9% saline solution for 10 minutes, their thickness measured, and the thickness expansion rate was calculated as follows:

Thickness Expansion Rate (%)=[thickness after liquid absorption (mm)/thickness before liquid absorption (mm)]×100

The weight of the above-prepared foams was measured, they were immersed in a 0.9% saline solution for 10 minutes, the weight of foams with liquid absorption was measured, and the degree of liquid absorption was calculated as follows:

Degree of Liquid Absorption (g/g)=[Foam weight after liquid absorption (g)−Foam weight before liquid absorption (g)]/Foam weight before liquid absorption (g)

The thickness expansion rate and the degree of liquid absorption of the foams of Examples 2 to 4, and Comparative Examples 2 to 4 were measured, and the results are shown in Table 2 below.

TABLE 2

| | Ex. 2 | Ex. 3 | Ex. 4 | Comp. Ex. 2 | Comp. Ex. 3 | Comp. Ex. 4 |
|---|---|---|---|---|---|---|
| Compression Temperature (° C.) | Room Temp. | 40 | 60 | 80 | 100 | 120 |
| Thickness Expansion Rate (%) | 1333 | 2000 | 1500 | 1250 | 1000 | 125 |
| Degree of Liquid Absorption (g/g) | 21.55 | 23.56 | 26.57 | 14.91 | 7.82 | 1.40 |

As shown in Table 2, both thickness expansion rate and the degree of liquid absorption were shown to be excellent when the compression was performed at 60° C. or below. When the compression temperature was above 60° C., both thickness expansion rate and the degree of liquid absorption dropped, and the thickness expansion rate was significantly reduced at 120° C. Accordingly, it was confirmed that compression should be preferably performed at 60° C. or below.

Experimental Example 3: Analysis of Characteristics According to Treatment with Dispersion Containing CMC in Liquid For the analysis of characteristics of CMC foams during the CMC foam preparation, when CMC foams are additionally immersed in a dispersion containing CMC in liquid between acid treatment and compression, the degree of liquid absorption under compression of the foams prepared in Examples 1 to 5 (untreated with a dispersion containing CMC in liquid) and Examples 6 to 10 (treated with a dispersion containing CMC in liquid) was measured, and compared.

The degree of liquid absorption under pressure of the above-prepared foams was calculated as shown below, after measuring both the weight of the above-prepared foams before liquid absorption and the weight of the above-prepared foams after immersing them in a 0.9% saline solution for 10 minutes followed by 40 mmHg of pressure thereon for 1 minute after liquid absorption:

Degree of Liquid Absorption Under Pressure (g/g)=
[Weight of wet foam after pressure (g)−Weight
of foam before liquid absorption (g)]/Weight of
foam before liquid absorption (g)

The degree of liquid absorption under pressure of the foams prepared in Examples 1 to 10 was measured and calculated as described above, and the results are shown in Table 3 below.

TABLE 3

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Acid for Treatment | HCl | Lactic acid | Lactic acid | Lactic acid | Citric acid | HCl | Lactic acid | Lactic acid | Lactic acid | Citric acid |
| CMC powder Treatment | x | x | x | x | x | ○ | ○ | ○ | ○ | ○ |
| Degree of Liquid Absorption Under Pressure (%) | 14.95 | 10.77 | 7.78 | 8.57 | 9.42 | 17.00 | 16.00 | 14.00 | 13.00 | 13.00 |
| Degree of Liquid Absorption (%) | 42.05 | 21.55 | 23.56 | 26.57 | 28.61 | 35.67 | 33.27 | 34.33 | 35.83 | 33.03 |
| Thickness Expansion Rate (%) | 1200 | 1333 | 2000 | 1500 | 942 | 1200 | 1571 | 1111 | 1667 | 968 |

As shown in the above table, even when treated under the same acid, the foams, which were additionally treated with a dispersion containing CMC in liquid, were shown to have higher degree of liquid absorption under pressure. That is, when foams were coated with CMC by additional treatment with a dispersion containing CMC in liquid, the amount being leached out was reduced, even when they were subjected to pressure.

What is claimed is:

1. A water-insoluble carboxymethyl cellulose foam that does not gelate when absorbing liquid, wherein the foam has a degree of liquid absorption of 20 g/g or higher when applied a 0.9% saline solution, and has a 2-fold or higher expansion in volume after absorption of the saline solution compared to that before absorbing the saline solution.

2. The foam of claim 1, wherein the foam has a 3-fold or higher expansion in volume after absorption of the saline solution compared to that before absorbing the saline solution.

3. The foam of claim 1, wherein the foam has a 4-fold or higher expansion in volume after absorption of the saline solution compared to that before absorbing the saline solution.

4. A method of preparing the water-insoluble carboxymethyl cellulose foam that does not gelate when absorbing liquid, according to claim 1, the method comprising:
(1) preparing a carboxymethyl cellulose foam by freeze-drying a solution in which 1 wt % to 2 wt % of carboxymethyl cellulose powder is dissolved;
(2) acid-treating the foam prepared in step (1) by immersing the foam in an acid solution, and then heating; and
(3) compressing the acid-treated foam in step (2) at 60° C. or below.

5. The method of claim 4, wherein the carboxymethyl cellulose solution in step (1) is an aqueous solution.

6. The method of claim 4, wherein the heating in step (2) is performed at from 40° C. to 70° C.

7. The method of claim 4, wherein the acid solution is prepared by adding an acid to a mixture containing an alcohol and water or adding an acid to an alcohol, and the acid is at least one selected from the group consisting of lactic acid, acetic acid, citric acid, succinic acid, formic acid, and hydrochloric acid.

8. The method of claim 7, wherein the volume of the alcohol in the mixture containing an alcohol and water accounts for 60% to 100% of the total volume of the mixture.

9. The method of claim 4, further comprising step (2-1) of immersing the acid-treated foam in the dispersion containing carboxymethyl cellulose powder in liquid, between step (2) and step (3).

10. The method of claim 9, wherein the liquid is selected from the group consisting of ethanol, methanol, and isopropanol.

11. The method of claim 4, wherein the foam has a 3-fold or higher expansion in volume after absorption of the saline solution compared to that before absorbing the saline solution.

12. The method of claim 4, wherein the foam has a 4-fold or higher expansion in volume after absorption of the saline solution compared to that before absorbing the saline solution.

13. A water-insoluble carboxymethyl cellulose foam that does not gelate when absorbing liquid, prepared by (i) freeze-drying a solution of carboxymethyl cellulose, thereby forming a carboxymethyl cellulose foam, (ii) acid-treating the carboxymethyl cellulose foam, thereby forming the water-insoluble carboxymethyl cellulose foam, and (iii) compressing the water-insoluble foam.

14. The foam of 13, wherein the water-insoluble carboxymethyl cellulose foam further comprises carboxymethyl cellulose powder in pores thereof, thereby improving the degree of liquid absorption or the degree of liquid absorption under pressure.

15. The foam of 13, wherein the degree of substitution of the carboxymethyl cellulose powder is 0.4 or higher.

* * * * *